United States Patent
Staszak et al.

(10) Patent No.: US 10,114,513 B2
(45) Date of Patent: Oct. 30, 2018

(54) SYSTEMS AND METHODS FOR PRINTING SENSOR CIRCUITS ON A SENSOR MAT FOR A STEERING WHEEL

(71) Applicant: TK Holdings Inc., Auburn Hills, MI (US)

(72) Inventors: Erick Staszak, Rochester Hills, MI (US); Dwayne Van'tZelfde, Holly, MI (US); Jason Lisseman, Shelby Township, MI (US)

(73) Assignee: JOYSON SAFETY SYSTEMS ACQUISITION LLC, Auburn Hills, MI (US)

( * ) Notice: Subject to any disclaimer, the term of this patent is extended or adjusted under 35 U.S.C. 154(b) by 0 days.

(21) Appl. No.: 14/728,366

(22) Filed: Jun. 2, 2015

(65) Prior Publication Data

US 2015/0344060 A1    Dec. 3, 2015

Related U.S. Application Data (60) Provisional application No. 62/006,312, filed on Jun. 2, 2014.

(51) Int. Cl.
*G01R 27/26* (2006.01)
*G06F 3/044* (2006.01)
(Continued)

(52) U.S. Cl.
CPC .......... *G06F 3/044* (2013.01); *G01N 27/041* (2013.01); *G06F 3/0488* (2013.01);
(Continued)

(58) Field of Classification Search
CPC ............. G01N 27/041; H03K 17/9622; H03K 2217/960765; H03K 2217/960755; G06F 3/044; G06F 3/0488; G06F 3/04883
(Continued)

(56) References Cited

U.S. PATENT DOCUMENTS

| 3,585,626 A | 6/1971 | Tartarini |
| 4,484,026 A | 11/1984 | Thornburg |

(Continued)

FOREIGN PATENT DOCUMENTS

| CN | 1988055 A | 6/2007 |
| CN | 201371849 Y | 12/2009 |

(Continued)

OTHER PUBLICATIONS

International Search Report, dated Sep. 2, 2015, received in connection with International Application No. PCT/US2015/033708.

(Continued)

*Primary Examiner* — Amy He
(74) *Attorney, Agent, or Firm* — Meunier Carlin & Curfman LLC (57) ABSTRACT

Systems and methods of printing sensor loops on a sensor mat for use in a steering wheel are disclosed herein. For example, the sensor mat may include a base substrate, one or more printed sensing loops, and an insulating material. The printed sensing loops are made with conductive ink that is disposed upon the base substrate or the insulating layer from a print head and adheres thereto. These sensor mats are versatile with respect to the type of base substrate and insulating materials that may be used, the shape of the sensing loops, and the area each loop may occupy. Shielding loop(s) may also be printed adjacent the sensing loop(s). This configuration allows shielding for the sensing loops as part of the sensing mat, which may reduce the thickness of the steering wheel rim and manufacturing and installation times.

33 Claims, 7 Drawing Sheets

(51) Int. Cl.
  *G01N 27/04* (2006.01)
  *G06F 3/0488* (2013.01)
  *H03K 17/96* (2006.01)
(52) U.S. Cl.
  CPC ..... *G06F 3/04883* (2013.01); *H03K 17/9622* (2013.01); *H03K 2217/960755* (2013.01); *H03K 2217/960765* (2013.01)
(58) Field of Classification Search
  USPC .......................... 345/173, 174; 324/658, 663
  See application file for complete search history.

(56) References Cited

U.S. PATENT DOCUMENTS

| | | |
|---|---|---|
| 4,540,979 A | 9/1985 | Gerger |
| 4,556,845 A | 12/1985 | Strope et al. |
| 4,631,976 A | 12/1986 | Noda et al. |
| 4,801,771 A | 1/1989 | Mizuguchi et al. |
| 4,929,934 A | 5/1990 | Ueda et al. |
| 5,398,962 A | 3/1995 | Kropp |
| 5,423,569 A | 6/1995 | Reighard et al. |
| 5,453,941 A | 9/1995 | Yoshikawa |
| 5,463,258 A | 10/1995 | Filion et al. |
| 5,539,259 A | 7/1996 | Filion et al. |
| 5,563,354 A | 10/1996 | Kropp |
| 5,793,297 A | 8/1998 | Takeuchi et al. |
| 5,871,063 A | 2/1999 | Young |
| 5,914,658 A | 6/1999 | Arakawa |
| 5,964,478 A | 10/1999 | Stanley et al. |
| 5,965,952 A | 10/1999 | Podoloff et al. |
| 6,016,103 A | 1/2000 | Leavitt |
| 6,172,610 B1 | 1/2001 | Prus |
| 6,239,409 B1 | 5/2001 | Bonn |
| 6,326,593 B1 | 12/2001 | Bonn |
| 6,333,736 B1 | 12/2001 | Sandbach |
| 6,365,875 B1 | 4/2002 | Kreuzer |
| 6,378,384 B1 | 4/2002 | Atkinson et al. |
| 6,392,542 B1 | 5/2002 | Stanley et al. |
| 6,495,799 B1 | 12/2002 | Pillsbury |
| 6,501,463 B1 | 12/2002 | Dahley et al. |
| 6,590,499 B1 | 7/2003 | D'Agosto |
| 6,661,345 B1 | 12/2003 | Bevan |
| 6,703,845 B2 | 3/2004 | Stanley et al. |
| 6,906,700 B1 | 6/2005 | Armstrong |
| 6,918,610 B2 | 7/2005 | Song et al. |
| 7,126,583 B1 | 10/2006 | Breed |
| 7,321,311 B2 | 1/2008 | Rieth |
| 7,649,278 B2 | 1/2010 | Yoshida et al. |
| 7,687,747 B2 | 3/2010 | Lee |
| 7,688,213 B2 | 3/2010 | Power |
| 7,763,187 B1 * | 7/2010 | Veedu .................. C09D 11/03 252/503 |
| 7,830,265 B2 | 11/2010 | Power |
| 7,908,941 B2 | 3/2011 | Menaldo |
| 7,928,341 B2 | 4/2011 | Ito et al. |
| 8,011,234 B2 | 9/2011 | Kandler |
| 8,095,270 B2 | 1/2012 | Bossler et al. |
| 8,203,454 B2 | 6/2012 | Knight et al. |
| 8,214,105 B2 | 7/2012 | Daly et al. |
| 8,269,731 B2 | 9/2012 | Molne |
| 8,461,957 B2 * | 6/2013 | Haag ................ B29C 45/14639 174/257 |
| 8,564,424 B2 | 10/2013 | Evarts et al. |
| 8,698,764 B1 | 4/2014 | Karakotsios et al. |
| 8,952,907 B2 | 2/2015 | Brown et al. |
| 8,970,231 B2 | 3/2015 | Kandler |
| 8,970,232 B2 | 3/2015 | Kandler |
| 8,983,732 B2 | 3/2015 | Bosch et al. |
| 9,007,190 B2 | 4/2015 | Bosch et al. |
| 9,643,560 B2 | 5/2017 | Honmatsu et al. |
| 2001/0030182 A1 | 10/2001 | Haag |
| 2002/0036119 A1 | 3/2002 | Bonn et al. |
| 2002/0054060 A1 | 5/2002 | Schena |
| 2003/0043014 A1 | 3/2003 | Nakazawa et al. |
| 2003/0074092 A1 | 4/2003 | Carrabis |
| 2003/0076968 A1 | 4/2003 | Rast |
| 2003/0083131 A1 | 5/2003 | Armstrong |
| 2003/0111453 A1 | 6/2003 | Haag et al. |
| 2004/0144197 A1 | 7/2004 | O'Grady |
| 2004/0155020 A1 | 8/2004 | Worrell |
| 2004/0212189 A1 | 10/2004 | Kachu |
| 2004/0267422 A1 | 12/2004 | Bossler |
| 2005/0052426 A1 | 3/2005 | Hagermoser et al. |
| 2005/0067889 A1 | 3/2005 | Chernoff et al. |
| 2005/0260492 A1 * | 11/2005 | Tucholski ......... H01M 10/0436 429/185 |
| 2005/0273218 A1 | 12/2005 | Breed et al. |
| 2006/0025897 A1 | 2/2006 | Shostak et al. |
| 2006/0054479 A1 | 3/2006 | Iisaka et al. |
| 2006/0066085 A1 | 3/2006 | Durocher |
| 2006/0109256 A1 | 5/2006 | Grant et al. |
| 2006/0113880 A1 | 6/2006 | Pei et al. |
| 2006/0177212 A1 | 8/2006 | Lamborghini et al. |
| 2006/0231320 A1 | 10/2006 | Kamizono et al. |
| 2006/0248478 A1 | 11/2006 | Liau |
| 2006/0262103 A1 | 11/2006 | Hu et al. |
| 2006/0284839 A1 | 12/2006 | Breed et al. |
| 2007/0029768 A1 | 2/2007 | Clos et al. |
| 2007/0062753 A1 | 3/2007 | Yoshida et al. |
| 2007/0100523 A1 | 5/2007 | Trachte |
| 2007/0187134 A1 | 8/2007 | Detian |
| 2007/0210050 A1 | 9/2007 | Choi |
| 2007/0278214 A1 | 12/2007 | Weiss |
| 2008/0042856 A1 | 2/2008 | Power |
| 2008/0061954 A1 | 3/2008 | Kulas |
| 2008/0079604 A1 | 4/2008 | Madonna et al. |
| 2008/0085021 A1 | 4/2008 | Shim |
| 2008/0202912 A1 | 8/2008 | Boddie et al. |
| 2008/0210048 A1 | 9/2008 | Yoneyama et al. |
| 2009/0001855 A1 | 1/2009 | Lipton et al. |
| 2009/0009480 A1 | 1/2009 | Heringslack |
| 2009/0032524 A1 | 2/2009 | Li |
| 2009/0140994 A1 | 6/2009 | Tanaka et al. |
| 2009/0151447 A1 | 6/2009 | Jin et al. |
| 2009/0160529 A1 | 6/2009 | Lamborghini et al. |
| 2009/0241378 A1 | 10/2009 | Ellis |
| 2010/0045454 A1 | 2/2010 | Knight et al. |
| 2010/0045612 A1 | 2/2010 | Moline |
| 2010/0053087 A1 | 3/2010 | Dai et al. |
| 2010/0071502 A1 | 3/2010 | Yasuda |
| 2010/0096159 A1 | 4/2010 | Abe |
| 2010/0102972 A1 | 4/2010 | Middlekauff et al. |
| 2010/0130808 A1 | 5/2010 | Hattori |
| 2010/0168998 A1 | 7/2010 | Matsunaga |
| 2010/0200268 A1 | 8/2010 | Suzuki |
| 2010/0231239 A1 | 9/2010 | Tateishi et al. |
| 2010/0250071 A1 | 9/2010 | Pala et al. |
| 2010/0268426 A1 | 10/2010 | Pathak et al. |
| 2010/0277186 A1 | 11/2010 | Bieck et al. |
| 2010/0315267 A1 | 12/2010 | Chung et al. |
| 2011/0016868 A1 | 1/2011 | Oda |
| 2011/0037721 A1 | 2/2011 | Cranfill |
| 2011/0046788 A1 | 2/2011 | Daly et al. |
| 2011/0054359 A1 | 3/2011 | Sazonov et al. |
| 2011/0073384 A1 | 3/2011 | Osoinach |
| 2011/0115617 A1 | 5/2011 | Bennett |
| 2011/0133919 A1 | 6/2011 | Evarts et al. |
| 2011/0175844 A1 | 7/2011 | Berggren |
| 2011/0189890 A1 | 8/2011 | Lee et al. |
| 2011/0210926 A1 | 9/2011 | Pasquero et al. |
| 2011/0216015 A1 | 9/2011 | Edwards |
| 2011/0241850 A1 | 10/2011 | Bosch et al. |
| 2011/0245992 A1 | 10/2011 | Stahlin et al. |
| 2011/0246028 A1 | 10/2011 | Lisseman et al. |
| 2011/0257846 A1 | 10/2011 | Bennett |
| 2011/0290038 A1 | 12/2011 | Hoshino et al. |
| 2012/0038468 A1 | 2/2012 | Provancher |
| 2012/0126965 A1 | 5/2012 | Sanma et al. |
| 2012/0179328 A1 | 7/2012 | Goldman-Shenhar |
| 2012/0232751 A1 | 9/2012 | Guspan |
| 2012/0296528 A1 | 11/2012 | Wellhoefer et al. |
| 2012/0306512 A1 | 12/2012 | Kandler |
| 2012/0326735 A1 | 12/2012 | Bennett et al. |

(56) References Cited

U.S. PATENT DOCUMENTS

| | | |
|---|---|---|
| 2013/0027065 A1 | 1/2013 | Stanley et al. |
| 2013/0120052 A1 | 5/2013 | Siska |
| 2013/0277351 A1 | 10/2013 | Lamesch |
| 2014/0054880 A1 | 2/2014 | Feinstein |
| 2014/0076063 A1 | 3/2014 | Lisseman et al. |
| 2014/0092025 A1 | 4/2014 | Pala et al. |
| 2014/0151356 A1 | 6/2014 | Maquire et al. |
| 2014/0224040 A1 | 8/2014 | Van'tZelfde et al. |
| 2014/0253151 A1 | 9/2014 | Kandler et al. |
| 2014/0331815 A1* | 11/2014 | Rispoli .......... B62D 1/06 74/558 |
| 2015/0054317 A1 | 2/2015 | Fortune et al. |
| 2015/0205421 A1 | 7/2015 | Lin et al. |
| 2016/0176037 A1 | 6/2016 | Hirai |

FOREIGN PATENT DOCUMENTS

| | | |
|---|---|---|
| CN | 102745231 | 10/2012 |
| DE | 202004020425 | 8/2005 |
| DE | 102009058138 | 6/2006 |
| DE | 102005024432 | 10/2006 |
| DE | 102007024141 | 11/2008 |
| DE | 102011006448 | 10/2011 |
| DE | 102012000572 | 7/2013 |
| JP | 61-146671 | 7/1986 |
| JP | 61-146670 | 9/1986 |
| JP | 09226597 | 9/1997 |
| JP | 2000228126 | 8/2000 |
| JP | 2002538044 A | 11/2002 |
| JP | 2007114122 | 5/2007 |
| JP | 2008-059459 | 3/2008 |
| JP | 2010-026610 | 2/2010 |
| JP | 2011-063103 | 3/2011 |
| JP | 2011219085 | 11/2011 |
| JP | 2013505865 | 2/2013 |
| WO | 9638325 A1 | 12/1996 |
| WO | 2011016868 | 10/2011 |
| WO | 2014130188 A1 | 8/2014 |

OTHER PUBLICATIONS

Written Opinion, dated Sep. 2, 2015, received in connection with International Application No. PCT/US2015/033708.
International Search Report, dated Aug. 28, 2015, received in connection with International Application No. PCT/US2015/032116.
Written Opinion, dated Aug. 28, 2015, received in connection with International Application No. PCT/US2015/032116.
International Preliminary Report on Patentability and Written Opinion, dated Aug. 18, 2015, received in connection with PCT/US2014/016023.
International Search Report and Written Opinion, dated May 23, 2014, received in connection with International Application No. PCT/US2014/016023.
Office Action, dated Jun. 30, 2015, received in connection with JP Application No. 2011-082736. (English Translation).
Office Action, dated Nov. 4, 2014, received in connection with JP Application No. 2011-082736. (English Translation).
U.S. Appl. No. 14/178,578, filed Feb. 12, 2014.
Notice of Allowance, dated Sep. 25, 2015, received in connection with U.S. Appl. No. 14/178,578, filed Feb. 12, 2014.
Non Final Office Action in U.S. Appl. No. 14/178,578 dated May 11, 2015.
U.S. Appl. No. 13/078,793, filed Apr. 1, 2011 (U.S. Pat. No. 8,983,732, issued Mar. 17, 2015).
Notice of Allowance, dated Nov. 3, 2014, received in connection with U.S. Appl. No. 13/078,793, filed Apr. 1, 2011 (now U.S. Pat. No. 8,983,732, issued Mar. 17, 2015).
Final Office Action in U.S. Appl. No. 13/078,793 dated May 6, 2014.
Non Final Office Action in U.S. Appl. No. 13/078,793 dated Dec. 16, 2013.
Non Final Office Action in U.S. Appl. No. 13/078,793 dated Dec. 6, 2012.
Final Office Action in U.S. Appl. No. 13/078,793 dated Jun. 3, 2013.
Final Office Action in U.S. Appl. No. 13/078,793 dated Mar. 15, 2013.
U.S. Appl. No. 13/076,226, filed Mar. 30, 2011 (U.S. Pat. No. 9,007,190, issued Apr. 14, 2015).
Supplemental Notice of Allowance, dated Feb. 20, 2015, received in connection with U.S. Appl. No. 13/076,226.
Notice of Allowance, dated Dec. 23, 2014, received in connection with U.S. Appl. No. 13/076,226.
Non Final Office Action in U.S. Appl. No. 13/076,226 dated Sep. 11, 2014.
Final Office Action in U.S. Appl. No. 13/076,226 dated Feb. 13, 2014.
Non Final Office Action in U.S. Appl. No. 13/076,226 dated Mar. 11, 2013.
U.S. Appl. No. 14/719,480, filed May 22, 2015.
International Preliminary Report on Patentability and Written Opinion, dated Apr. 22, 2014, in connection with corresponding International Application No. PCT/EP2012/070777.
"Modellierung und Realisierung eines digitalen Trägerfrequenzmesssystems zur Messung von kapazitiven Sensoren im Umfeld einer Ultrapräzisionsdrehmaschine" Dipl.-Ing. Jonas Bluth aus Rutesheim "Modeling and realization of a digital Carrier frequency measuring system for the measurement of capacitive sensors in the Environment of an ultra-precision turning machine"—Dissertation by Jonas Bluth—English abstract included.
Office Action issued in co-pending U.S. Appl. No. 14/353,109, dated Apr. 21, 2016.
Office Action issued in co-pending U.S. Appl. No. 14/353,109, dated Sep. 15, 2016.
Office Action issued in co-pending U.S. Appl. No. 14/353,109, dated Feb. 23, 2017.
Office Action issued in Chinese Application No. 201480008587.9, dated Oct. 9, 2016, English translation included.
International Preliminary Report on Patentability issued for International Application No. PCT/US15/32116, dated Nov. 22, 2016.
International Preliminary Report on Patentability issued in PCT/US15/33708, dated Dec. 6, 2016.
Office Action issued in co-pending U.S. Appl. No. 14/719,480, dated Apr. 26, 2018.
Comeford, "Proximity Sensing Solutions, Part 1: Capacitive Sensors", DigiKey Electronics, Sep. 19, 2013, 3 pages.
Office Action issued for Chinese Application No. 201580027253, dated Jun. 27, 2018.
Office Action issued for Chinese Application No. 201580029042, dated May 28, 2018.

\* cited by examiner

SYSTEMS AND METHODS FOR PRINTING SENSOR CIRCUITS ON A SENSOR MAT FOR A STEERING WHEEL

CROSS REFERENCE TO RELATED APPLICATIONS

This application claims priority to U.S. Provisional Patent Application No. 62/006,312, entitled "Systems and Methods for Printing Sensor Circuits on a Sensor Mat for a Steering Wheel," filed Jun. 2, 2014, the contents of which is herein incorporated by reference in its entirety.

BACKGROUND

Current steering wheel designs may include one or more sensor mats around a rim of the steering wheel frame that are configured for detecting the presence of a driver's hand using capacitive-type sensing. Known sensor mats include a wire loop that is sewn to a fabric or foam substrate.

The steering wheel frame is typically made of metal, such as a magnesium alloy or steel and can be a source of interference for the signal(s) in the sensing mat.

Thus, existing sensor mats may be time consuming to manufacture, which includes designing a wire stitch layout for the sensor and designing the wire stitch layout for the shield, each being on separate mats that must fit correctly over the complex curve shape of the steering wheel rim. In addition, the pattern may need to be redesigned depending on which areas should provide sensing and the vehicle manufacturer's steering wheel specifications, which can be time consuming. Furthermore, the manufacturing process and available materials limits the ability to use the available space on the base substrate.

Accordingly, there is a need in the art for an improved sensor mat and method for making the same.

BRIEF SUMMARY

Systems and methods of printing sensor loops, or circuits, on a sensor mat for use in a steering wheel are disclosed herein. In particular, a sensor mat according to various implementations includes a base substrate, one or more printed sensing loops, and a dielectric or insulating material. The printed sensing loops are made with conductive ink that is disposed upon the base substrate or the insulating layer from a print head, for example, and adheres thereto. These sensor mats are versatile with respect to the type of base substrate and insulating material used and the shape of the sensing loops and the area each loop occupies. In addition, in certain implementations, the sensor mats include one or more printed shielding loops adjacent the sensing loops and separated from the sensing loops by a layer of insulating material. The thickness of the insulating material, which separates the sensor from the shield, can be specified based on the sensor/shield layout configuration. Increasing the thickness can help reduce noise effects between the sensor and shield and also prevent 'effective shorting' due to construction variation. This configuration allows shielding for the sensing loops as part of the sensing mat, which may reduce unwanted electrical interference with the electrical signal(s) carried by the sensor mat caused by the sensor mats proximity with the steering wheel rim, the thickness of the steering wheel rim, and manufacturing and installation times.

According to various implementations, the conductive ink may include silver, carbon, carbon nanotube (CNT), graphene, or copper. In addition, the base substrate may include a polymer foam, a polymer film, leather, vinyl, felt, or non-woven material. The insulating materials may include any suitable dielectric or insulating material, such as polyamides, or other printable dielectric inks.

In one implementation, the one or more sensing loops are printed onto the base substrate. The insulating material is a first insulating material, and one or more shielding loops are printed with the conductive ink onto the first insulating material. A second insulating material is disposed over the one or more shielding loops. The one or more sensing loops include a first sensing loop and a second sensing loop, and the one or more shielding loops include a first shielding loop and a second shielding loop. The first shielding loop is disposed adjacent the first sensing loop, and the second shielding loop is disposed adjacent the second sensing loop. However, in an alternative implementation, the first shielding loop may be disposed adjacent the first and second sensing loops.

The sensor mat may further include one or more shielding feed traces printed with conductive ink onto the first insulating material. Each shielding feed trace extends from a corresponding shielding loop toward an edge of the first insulating material. The sensor mat may also include one or more sensor return traces printed with conductive ink onto the base substrate. The sensor return traces extend from a corresponding sensing loop toward an edge of the base substrate.

In an alternative implementation, one or more shielding loops are printed with conductive ink onto a second insulating material disposed over the base substrate. The insulating material disposed over the sensing loops is a first insulating material, and a third insulating material is disposed over the one or more shielding loops. The one or more sensing loops are printed onto the third insulating material.

In addition, according to various implementations, a system for hand sensing on a steering wheel includes a sensor mat, such as the sensor mats described above, and an electronic control unit (ECU) that is in communication with the sensor mat. The ECU includes a processor and a power source. The processor is configured for receiving a signal from at least one of the one or more sensing loops and determining an indication associated with the signal.

In certain implementations in which the sensor mat includes one or more shielding loops and shielding feed traces, the system includes shielding feed wires that extend between the ECU and the respective shielding feed traces. The processor is configured for instructing the power source to selectively generate a voltage signal through the one or more shielding loops via the shielding feed wires and the shielding feed traces. The system may also include sensor return wires that extend between the ECU and the respective sensor return traces. The signal received from at least one of the sensing loops is received by the processor via the sensor return wire and the sensor return trace.

According to other various implementations, a method of manufacturing a sensor mat includes (1) printing one or more sensing loops with conductive ink adjacent a base substrate that is configured for being installed around the steering wheel frame rim and (2) disposing a layer of insulating material over the one or more sensing loops. In one implementation, printing the one or more sensing loops includes printing the one or more sensing loops on the base substrate. In this implementation, the insulating material is a first layer of insulating material, and the method also includes printing one or more shielding loops with conductive ink onto the first insulating layer and disposing a second layer of insulating material over the one or more shielding loops.

In an alternative implementation, the layer of insulating material is a first layer of insulating material, and the method includes printing one or more shielding loops with conductive ink onto a second insulating material disposed on the base substrate and disposing a third layer of insulating material over the one or more shielding loops. The one or more sensing loops are printed onto the third layer of insulating material.

The method may also include selectively generating a voltage signal through one or more of the shielding loops that are disposed adjacent the sensing loops. The voltage signal is sufficient to shield the adjacent sensing loop from electrical interference from a metal steering wheel frame.

BRIEF DESCRIPTION OF THE DRAWINGS

The components in the drawings are not necessarily to scale relative to each other. Like reference numerals designate corresponding parts throughout the several views.

DETAILED DESCRIPTION

Systems and methods of printing sensor loops, or circuits, on a sensor mat for use in a steering wheel are disclosed herein. In particular, a sensor mat according to various implementations includes a base substrate, one or more printed sensing loops, and a dielectric or insulating material. The printed sensing loops are made with conductive ink that is disposed upon the base substrate or the insulating layer from a print head, for example, and adheres thereto. These sensor mats are versatile with respect to the type of base substrate and insulating material used and the shape of the sensing loops and the area each loop occupies. In addition, in certain implementations, the sensor mats include one or more printed shielding loops made with conductive ink adjacent the sensing loops and separated from the sensing loops by a layer of insulating material. The thickness of the insulating material, which separates the sensor from the shield, can be specified based on the sensor/shield layout configuration. Increasing the thickness can help reduce noise effects between the sensor and shield and also prevent 'effective shorting' due to construction variation. This configuration allows shielding for the sensing loops as part of the sensing mat, which may reduce unwanted electrical interference with the electrical signal(s) carried by the sensor mat caused by the sensor mats proximity with the steering wheel rim, the thickness of the steering wheel rim, and manufacturing and installation times.

To date, printed conductive inks have not been used in steering wheel sensor or heating mats because of the complex three-dimensional geometry of the steering wheel and the possibility of visual read-through on the top surface of the steering wheel. In addition, there is concern about the ink patterns breaking when the mat is stretched and/or wrapped tightly around the steering wheel frame rim and adjacent to spokes in the steering wheel frame. However, applicants have discovered various solutions for avoiding these issues. For example, according to one implementation, conductive inks having suitable elongation and flexibility characteristics may be printed onto a sufficiently stretchable base substrate, which allows the sensor mat to be stretched more evenly around the steering wheel frame rim and avoid undesirable bunching of the base substrate. According to another implementation, a polymeric foam layer may be disposed between the mat and the skin, which prevents read through. This implementation may be particularly useful when the stretchable ink and base substrate cannot be used for the particular steering wheel rim configuration and some bunching of the base substrate is unavoidable. And, according to yet another implementation, the base substrate onto which the conductive ink is printed may be the underside of the leather skin that is installed as the outermost layer of the steering wheel, which alleviates concerns about read through and further reduces the materials used in the manufacturing and installation process and the time and costs associated with installation. These and other implementations are discussed in more detail below in relation to FIGS. 3 through 11.

Figure 1A:
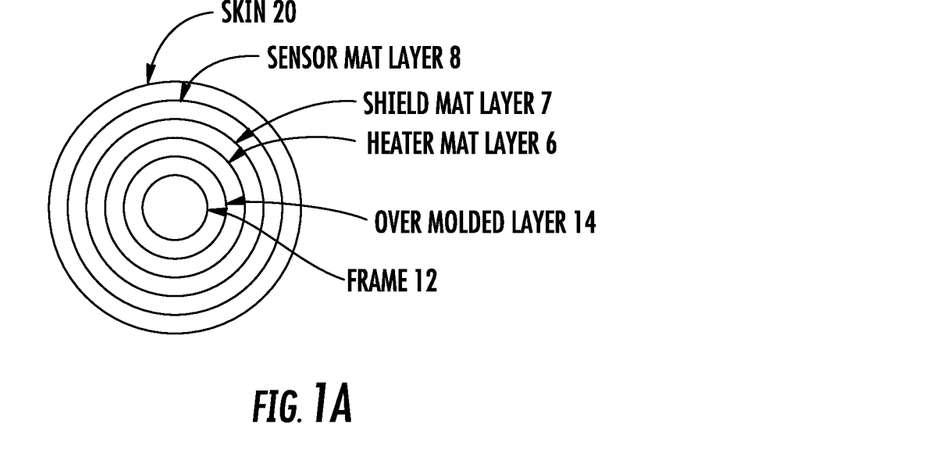
FIG. 1A illustrates a cross sectional view of layers in a steering wheel.
Figure 1B:
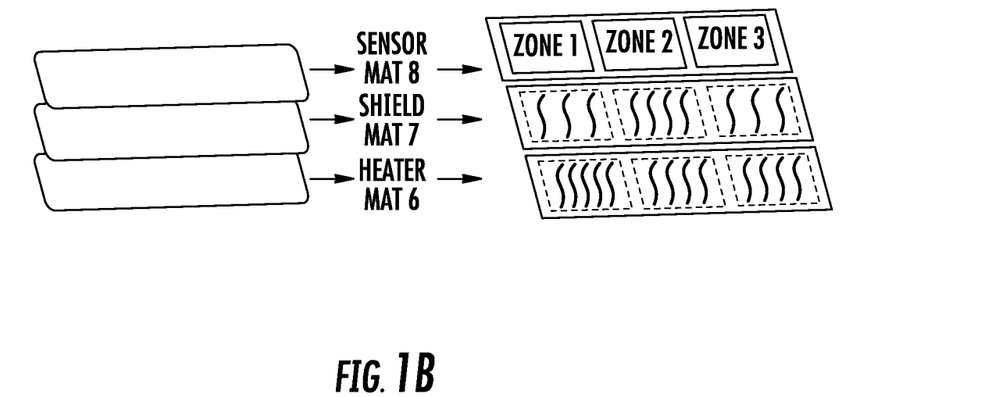
FIG. 1B illustrates a perspective view of a sensor mat layer with multiple zones and a shielding mat.

FIG. 1A illustrates a cross-sectional view of a steering wheel rim sensing system that includes a sensor mat, a shielding mat, and a heater mat. In particular, the rim includes a frame 12, a first over molded layer (e.g., foam) 14, the heater mat 6, the shield mat 7, the sensor mat 8, and an outer skin 20. Some sensor mat designs may include one sensing zone or multiple sensing zones that are spaced apart from each other. FIG. 1B illustrates a perspective view of a sensor mat that has more than one sensing zone and a separate shielding mat having more than one conductive zone that is disposed between the sensor mat and the steering wheel frame. Each conductive zone on the shielding mat shields the portion of the sensor mat that is adjacent to it.

Figure 2:
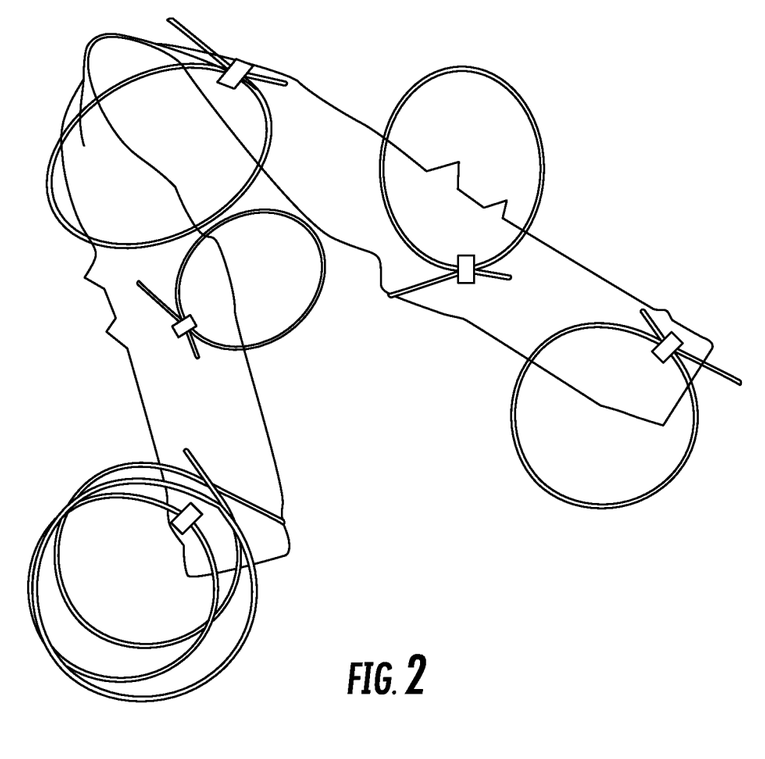
FIG. 2 illustrates a sensor mat.

Each wire loop having its own return trace (or return wire connected thereto) defines a discrete sensing circuit, or zone. FIG. 2 illustrates a perspective view of an exemplary sensor mat having this configuration. Sensor return wires that extend from the sensing zones may present an additional source of electrical interference for other sensing zones, particularly when the sensor return wire from one sensing zone is routed close to another sensing zone. To limit interference, attempts are made to route the sensor return wires to avoid the various zones, but this configuration is not always a viable option due to space limitations on the sensor mat and/or the configuration of the steering wheel. Applicants have also discovered systems and methods for selectively shielding one or more sensing loops at a time.

Figure 3:
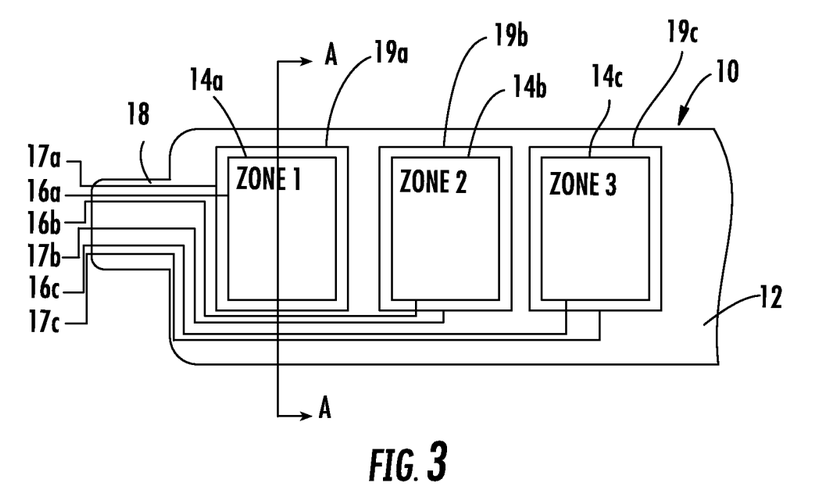
FIG. 3 illustrates a top view of a sensor mat according to one implementation.

For example, FIG. 3 illustrates a top view of a sensor mat 10 according to various implementations. The sensor mat 10 includes a base substrate 12, one or more sensing loops 14a, 14b, 14c that are printed with conductive ink on the base substrate 12, and a sensor return trace 16a, 16b, 16c printed on the base substrate 12 and extending between each sensing loop 14a-14c, respectively, and one end 18 of the base substrate 12. The one or more sensing loops 14a, 14b, 14c are responsive to input in the areas designated generally as "zone 1", "zone 2", and "zone 3", respectively. The area outlined designating each zone may have a suitable circuit pattern within the designated area. For example, the circuit pattern may have a substantially zigzag arrangement, a substantially spiral arrangement, a grid pattern arrangement, a cross-hatch arrangements, or a solid area arrangement.

In addition, in other implementations, there may be one or more zones, and these areas or circuit patterns may be shaped differently or disposed on other portions of the base substrate 12. The number, shape, and relative positions of the zones on the base substrate may be determined based on the sensing needs for the sensor mat 10 and the shape of the steering wheel for the particular vehicle. Furthermore, the conductive ink circuits that make up sensing loops 14a, 14b, 14c may extend over a portion of the general area of the zone but not necessarily cover substantially all of the zone.

As shown in FIG. 3, the sensor return traces 16a, 16b, 16c extend from one side of the sensing loop area 14a, 14b, 14c, respectively, and over a portion of the base substrate 12 that is not part of a sensing zone. Accordingly, the respective return traces 16a, 16b, 16c do not interfere with signals carried by each other. However, this layout may not be suitable for all steering wheel configurations. For example, as discussed below in relation to FIGS. 8 and 9, if more sensing zones are required or if different inputs are to be received from the one or more of the sensing zones, there may not be sufficient space available on the base substrate for printing the sensor return traces such that they do not extend over another sensor return trace or over another sensing loop area.

Figure 4:
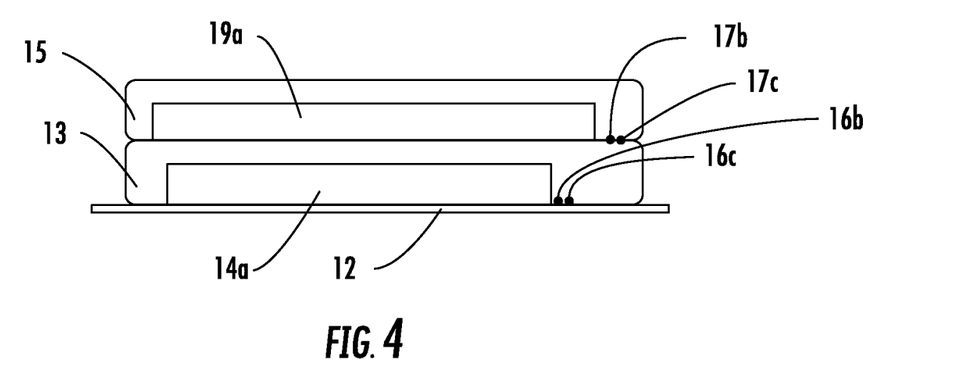
FIG. 4 illustrates a cross sectional view of the sensor mat in FIG. 3.

In addition, as shown in FIG. 4, the sensor mat 10 includes a first dielectric or insulating layer 13 disposed over the sensing loops 14a-14c and sensor return traces 16a-16c. One or more shielding loops 19a, 19b, and 19c are printed with conductive ink on the layer 13. The shielding loops 19a-19c extend over the area defined by the sensing loops 14a-14c and the sensor return traces 16a-16c, respectively. A shielding feed trace 17a, 17b, 17c extends between each shielding loop 19a, 19b, 19c, respectively, and the end 18 of the base substrate 12. A second dielectric or insulating layer 15 is disposed over the shielding loops 19a-19c and the shielding feed traces 17a-17c. Similar to the sensor return traces 16a-16c, the shielding feed traces 17a-17c extend adjacent the shielding loops 19a-19c but not over them.

The printing system used may include screen printing, ink jet printing, or pad printing, for example. The conductive ink may include conductive materials such as silver, carbon, CNT, graphene, copper, or other suitable conductive material. For example, according to various implementations, the conductive ink is able to elongate a minimum of about 10% without significant characteristic changes. In certain implementations, silver or carbon based inks (e.g., graphene) may be used because they can withstand at least 10% elongation without breakage or significant characteristic changes, such as changes in resistance. In addition, the conductive ink used for printing the sensing loops may be the same conductive ink used for printing the shielding loops, or different inks may be selected. Furthermore, the conductive material may be modified with additives, such as a polymer such as polyurethane, to affect the resistance.

Dielectric materials used may include polyamide-based material or other suitable insulating materials. In certain implementations, the insulating material may be the base substrate or a dielectric layer printed thereon and/or over printed sensing or shielding loops. In addition, the thickness of the insulating material may vary based on the density of the loop configuration adjacent to the insulating material. For example, the thickness may range from about 0.5 mm to about 1.0 mm or may be greater than or less than this range. Increasing the thickness can help reduce noise effects between the sensor and shield and also prevent 'effective shorting' due to construction variation. The base substrate may include felt, leather, a foam or film (e.g., polyurethane, polyethylene, or other suitable polymer), or other suitable non-woven materials capable of receiving and holding the printed conductive ink thereon. In various implementations, the base substrate has the ability to elongate between about 5% to about 20%. Substrates having a lower elongation tend to be more difficult to wrap around a steering wheel. As an example, top grain leather has an elongation characteristic of about 13±5% using a reference force (e.g., about 9 kg), and split grain leather has an elongation characteristic of about 5±3%.

The amount of stretching allowed by the substrate and the ink is taken into consideration when selecting the substrate, conductive ink, and the pattern of the loop(s) to prevent damage to the ink when the substrate is stretched around the steering wheel. In certain implementations, the conductive ink and the base substrate are selected such that the maximum elongation of the base substrate is substantially the same as the minimum elongation of the conductive ink. For example, in one implementation, a relatively stretchable non woven material, such as a non woven material having a maximum elongation of about 10% may be selected for the base substrate 12, and a graphene based ink having a minimum elongation of about 10% may be selected for the conductive ink. Also, depending on the shape to be wrapped around the steering wheel frame rim, the printed pattern may be selected to increase the robustness of the wrapping, elongation, and stretch processes required of the application. As a particular example, cross-hatching or zigzag patterns may be useful for this purpose.

Figure 5:
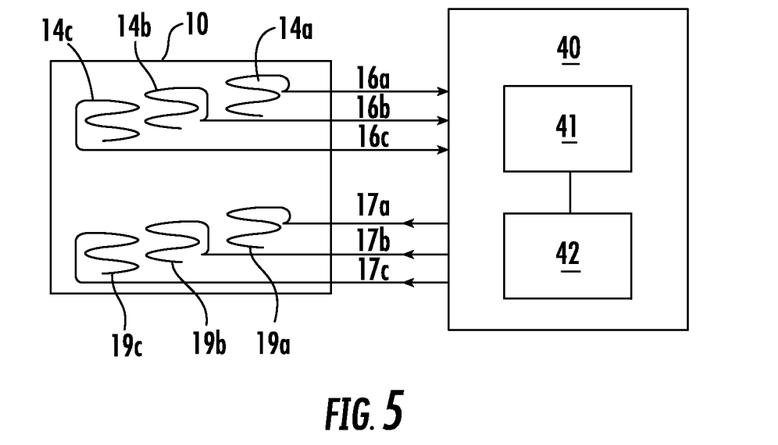
FIG. 5 illustrates a schematic view of a steering wheel system using the sensor mat shown in FIG. 3.

As shown in FIG. 5, the steering wheel system includes an electronic control unit 40 that includes a processor 41 and a power source 42. The ECU 40 is in electronic communication with one or more other vehicle systems (not shown) and the sensor mat 10 via the sensor return traces 16a-16c for the sensor loops 14a-14c, respectively, and shielding feed traces 17a-17c associated with each of the shielding loops 19a-19c, respectively.

The processor 41 is configured for detecting input from a driver, such as presence of a hand, adjacent each sensing loop 14a-14c. In one implementation, signals from one or more sensing loops 14a-14c are communicated to the processor 41 through sensor return traces 16a-16c, respectively, and sensor return wires (not shown separately) that extend from each sensor return trace 16a-16c to the ECU 40. For example, the signal may be generated through capacitance-type sensing in one or more of the sensing loops 14a-14c and received by the processor 41. The processor 41 may compare the signal to a range of signals that indicate various inputs. For example, the signals may be associated with various types of user input, such as a presence of a hand, a touch, a grip, a swipe motion, a tap motion, a double tap, a tap and hold, or a combination thereof from the signal received by the processor 41. The processor 41 may also control the level of current and/or frequency of the voltage signal generated by the power source 42 and when the level of current and/or the frequency of the voltage signal may be increased or decreased.

The power source 42 is configured for generating a voltage signal through the one or more shielding loops 19a-19c via one or more shielding feed wires that are connected to each of the one or more shielding feed traces 17a-17c, respectively. The voltage signal is configured for shielding the one or more sensor loops 14a, 14b, 14c that are adjacent the shielding loop(s) 19a, 19b, 19c. The shielding voltage signal may be a frequency-specific signal to shield the area adjacent the shielding loops 19a-19c. The frequency-specific signal of the shielding loops is configured for matching, as close as possible, the capacitance voltage signal generated for the respective sensing loops 14a-14c.

An electric current in the shielding loops may be less than about 200 microamperes. In certain implementations, the current may be between around 9 and around 11 microamperes, and in one implementation, the electrical current may be around 10 microamperes.

When installed in a steering wheel system, the sensor mat 10 is oriented such that the one or more shielding loops 19a-c are disposed between the steering wheel frame and the one or more sensing loops 14a-c.

Figure 6:
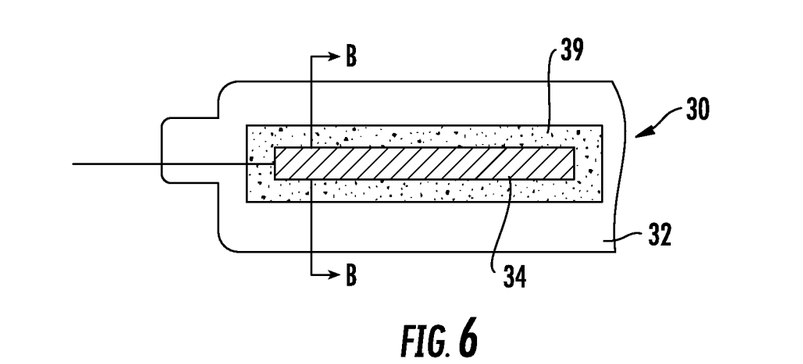
FIG. 6 illustrates a top view of a sensor mat according to another implementation.
Figure 7:
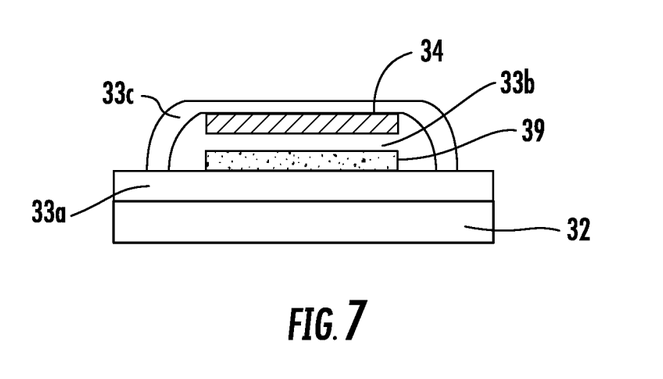
FIG. 7 illustrates a cross sectional view of the sensor mat in FIG. 6.

The implementation shown in FIGS. 6 and 7 is similar to the implementation described above in relation to FIGS. 3 and 4 but instead includes a shielding loop 39 printed directly onto a first dielectric or insulating layer 33a disposed on the base substrate 32 and a sensing loop 34 printed onto a second dielectric or insulating layer 33b disposed over the shielding loop 39. Alternatively (not shown), the shielding loop 39 may be printed onto the base substrate 32 if the base substrate 32 is a sufficient insulating material. The hatched area depicts the general area from which the sensing loop 34 receives input. The shielding loop 39 is depicted by the dotted area. A third dielectric or insulating layer 33c is disposed over the sensing loop 34. Similar to the implementation described above in relation to FIGS. 3 and 4, the sensor mat 30 is oriented such that the shielding loop 39 is disposed between the steering wheel frame and the sensing loop 34 when installed in the steering wheel system.

Figure 8:
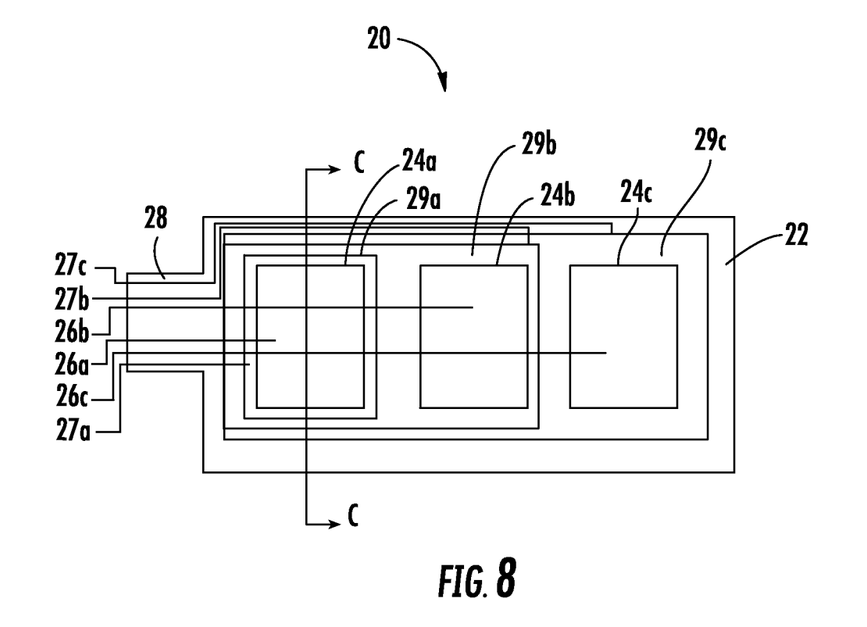
FIG. 8 illustrates a top view of a sensor mat according to another implementation.
Figure 9:
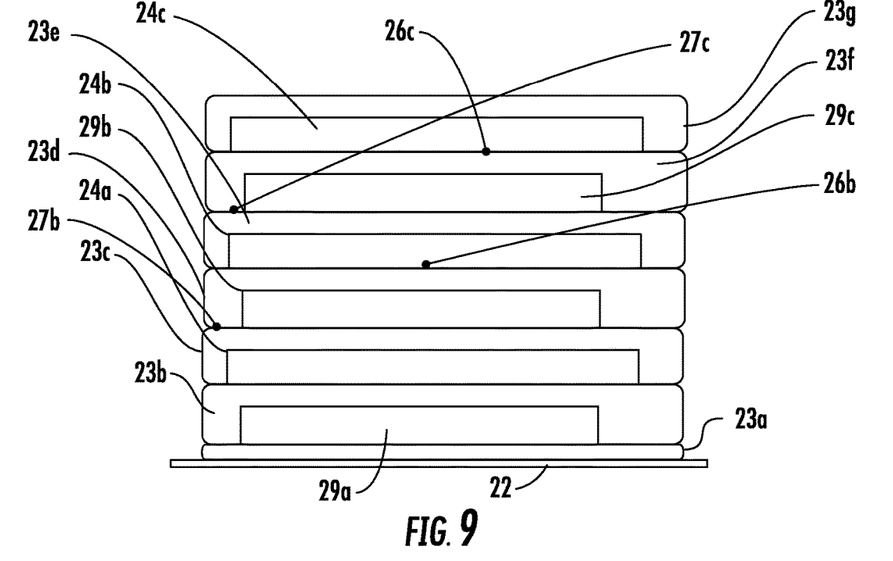
FIG. 9 illustrates a cross sectional view of the sensor mat in FIG. 8.

FIGS. 8 and 9 illustrate an implementation of a sensor mat 20 that includes dielectric layers, printed shielding loops, and printed sensing loops disposed in a stacked and vertically off-set arrangement such that shielding loops are provided between each sensor loop or sensor return trace to shield the signals therein. The sensor mat 20 includes a first dielectric layer 23a disposed directly onto the base substrate 22. A first shielding loop 29a its shielding feed trace 27a are printed on the first dielectric layer 23a. A second dielectric layer 23b is disposed over the first shielding loop 29a and trace 27a. A first sensing loop 24a and its corresponding sensor return trace 26a are printed on the second dielectric layer 23b above the first shielding loop 23a. A third dielectric layer 23c is disposed over the first sensing loop 24a and its sensor return trace 26a. A second shielding loop 29b and its corresponding shielding feed trace 27b are printed on the third dielectric layer 23c and next to the first shielding loop 29a when viewed from the top of the mat 20 (see FIG. 8). A fourth dielectric layer 24d is disposed over the second shielding loop 29b and its shielding feed trace 27b. A second sensing loop 24b and its sensor return trace 26b are printed on the fourth dielectric layer 24d above the second shielding loop 29b. A fifth dielectric layer 24e is disposed over the second sensing loop 24b and sensor return trace 26b. A third shielding loop 29c and its shielding feed trace 27c are printed on the fifth dielectric layer 24e next to the second shielding loop 29b as viewed from the top of the mat 20. A sixth dielectric layer 24f is disposed over the third shielding loop 29c and its shielding feed trace 27c. A third sensing loop 24c and its sensor return feed 26c are printed on the sixth dielectric layer 24f above the shielding loop 29c, and seventh dielectric layer 24g is disposed over the third sensing loop 24c and its sensor return trace 26c.

Having multiple, separate circuits of shielding loops 29a-29c allows the shielding loops 29a-29c to selectively shield one or more sensing zones. The shielding loops 29a-c receive voltage signals that prevent the steering wheel frame from interfering with the signals in the respective sensing loops 24a, 24b, 24c and the sensor return traces 26a, 26b, 26c. In other implementations (not shown), there may be other combinations of shielding loops and sensing loops.

Figure 10:
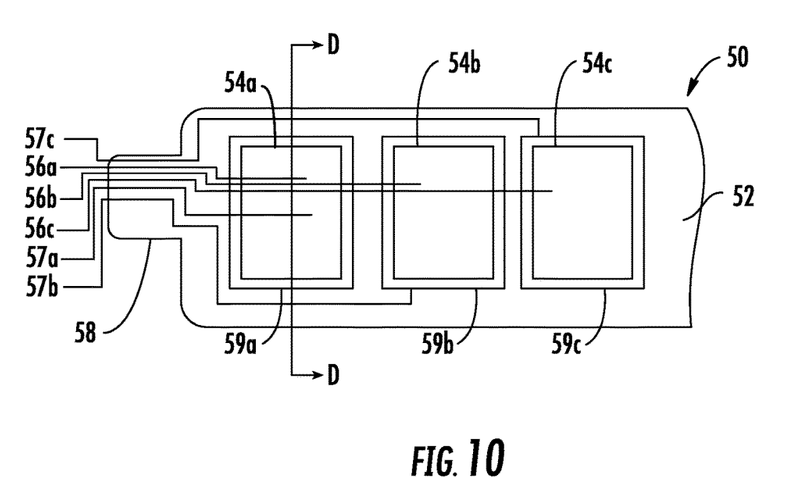
FIG. 10 illustrates a top view of a sensor mat layer according to another implementation.
Figure 11:
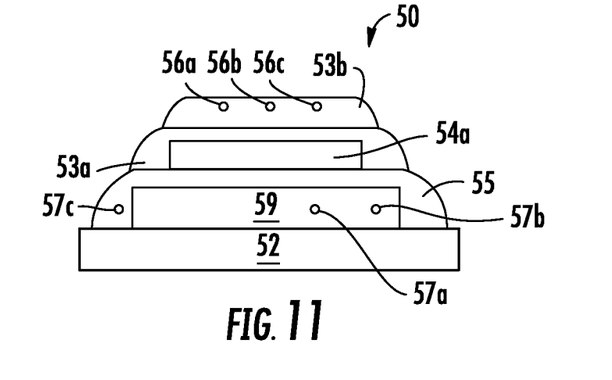
FIG. 11 illustrates a cross sectional view of the sensor mat in FIG. 10.

FIGS. 10 and 11 illustrate an alternative implementation that includes sensor return wires 56a-56c that are connected to the sensing loops 54a-54c, respectively, and extend upwardly through insulating material 53a disposed over the sensing loops 54a-54c. In particular, the sensor mat 50 includes shielding loops 59a-59c and shielding feed traces 57a-57c extending from the respective loops 59a-59c that are printed on the base substrate 22. In this implementation, the base substrate 22 acts as an insulating layer. A first dielectric or insulating layer 55 is disposed on the shielding loops 59a-59c and traces 57a-57c. Sensing loops 54a-54c are printed on the first insulating layer 55. Sensor return wires 56a, 56b, 56c are connected to sensing loops 54a, 54b, 54c, respectively, directly or via sensor return traces (not shown). A second dielectric or insulating layer 53a is disposed over the sensing loops 54a-54c, and the sensor return wires 56a-56c extend through and are laid above the second insulating layer 53a. A third dielectric or insulating layer 53b is disposed over the sensor return wires 56a-56c.

In alternative implementations (not shown), sensor return wires may be connected to printed sensor loops directly. In addition, the sensor return wires may be disposed in different dielectric or insulating layers from other sensor return wires. Furthermore, shield feed wires may be connected to the printed shielding feed traces or connected directly to the shielding loops. The shield feed wires may also be disposed in one or more dielectric or insulating layers that are separate from the shielding loops and other shield feed wires.

Sensor mats having sensor loops defined by an area of printed conductive ink and, optionally, shielding loops defined by an area of printed conductive ink, allow manufacturers more flexibility with the type of substrates that may be used, may reduce the thickness of the steering wheel rim, may be less time consuming to manufacture and install, and allow for some level of automation and customization in the shape of the sensing loops and the number of sensing loops that is not as easily achievable with current sensor mats. For example, the pattern of sensing loops to be printed may be repeated on multiple substrates, or it may be scaled up or down depending on the size of the substrates and needs of the vehicle manufacture. According to certain implementations, this technology allows custom patterns to be tuned from common stock print patterns, which reduces the time for design and production and increases the reliability of the production of the product.

In certain implementations in which a film base substrate is used, the total thickness of the sensor mat 20, 30, 50 may be between about 60 and about 185 microns. For example, the sensor layer, the dielectric layer for the sensor layer, the shield layer, and the dielectric layer for the shield layer each may be about 10 microns thick and the film substrate may be about 20 microns thick, resulting in a mat having an overall thickness of around 60 microns. In another implementation, the sensor layer and the shield layer each may be about 20 microns thick, the dielectric layers for the sensor and shield layers each may be about 10 microns thick, and the film substrate may be about 125 microns, resulting in a mat having an overall thickness of around 185 microns. In other implementations, a foam or a fabric substrate may be used. In such implementations, the foam substrate may have a thickness of up to about 1.5 mm and the fabric substrate may have a thickness of up to about 1 mm.

In various implementations, the sensor loops may be printed on materials that are already a part of the steering wheel assembly, which can reduce the overall thickness of the steering wheel rim and the materials used in the rim. For example, the sensor loops may be printed on the back of the leather or vinyl skin that makes up the outer layer of the steering wheel rim, for example. Or, the sensor loops may be printed on a surface of an over-molded polymeric foam layer included in the rim, as another example. In other implementations, sensor mats may be produced separately and installed by gluing or otherwise adhering the mats to the inside surface of the outer skin, which may reduce the time for installing the materials in the steering wheel rim and may increase the accuracy of the location of the one or more sensing zones along the steering wheel rim.

Figure 12:
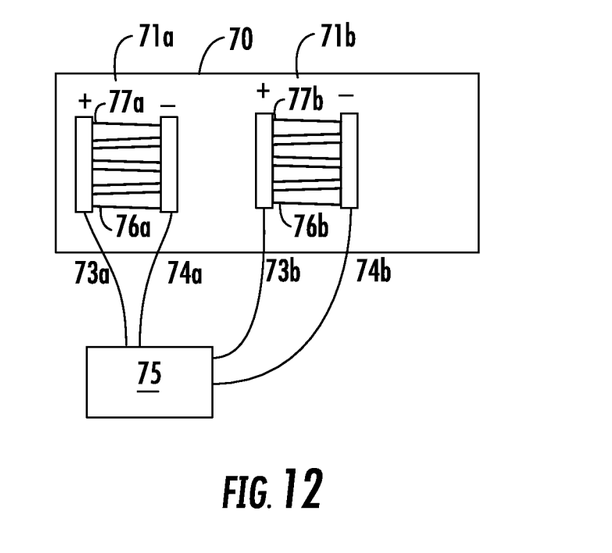
FIG. 12 illustrates a top view of a heater mat layer according to one implementation.

In addition, this technology may be applied to manufacturing heater mats for use in steering wheels. For example, FIG. 12 illustrates one implementation of a heater mat 70 manufactured by printing conductive ink onto a base substrate. The heater mat 70 includes one or more heating zones 71a, 71b that are each defined by a conductive loop, and supply 73a, 73b and return wires 74a, 74b extend between each conductive loop 71a, 71b, respectively, and power source 75. As shown, the pattern of ink for each of the heating zones 71a, 71b is at least in part selected to provide more even heating of the heater mat 70. In particular, a first portion 76a, 76b of zones 71a, 71b, respectively, are adjacent to where the supply wires 73a, 73b connect to the conductive supply trace of each zone, and a second portion 77a, 77b of each zone 71a, 71b, respectively, are disposed further away from the connection. The thickness of each portion 76a, 76b is less than the thickness of each portion 77a, 77b to provide greater resistance for the current flowing from each supply wire 73a, 73b into each loop 71a, 71b, respectively, which forces more of the current toward a distal portion of each conductive loop and provides for more even heating of each zone. The conductive ink is covered by a dielectric layer (not shown).

The power source 75 may be part of the same ECU, such as ECU 40 shown in FIG. 5, in communication with the sensing/shielding mat or it may be part of a separate ECU. In such implementations, the power source 75 can provide heating current to the heater mat 70 until the steering wheel reaches a predetermined temperature or until the power source 75 is otherwise instructed to stop generating current for the heater mat 70.

In addition, according to some implementations, the power source 75 may be the same power source used to generate the voltage signal for the shielding layer. In such an implementation, the power source is configured for selectively generating a voltage signal for the shielding layer and a heating current for the heater layer. The voltage signal may be configured to match, as close as possible, the voltage signal of the sensing loops, and a shielding current may be less than about 200 microamperes. The heating current may be between about 4 and about 8 amperes. For example, the power source may be configured for generating the heating current for one or more conductive loops of the heater layer in response to receiving an "on" signal for the heater. The on signal may be received from a presence signal from the one or more sensing loops indicating presence of a hand adjacent the one or more sensing loops or may be received from a button or other input device in the vehicle. In addition, the power source may be configured for generating the shielding voltage signal for one of the conductive zones of the shielding layer in response to receiving a signal (e.g., an override signal) indicating that sensing in one or more sensing zones, respectively, takes priority over heating. The power source may also configured for ceasing to generate the heating current for the one or more conductive loops of the heater layer in response to a temperature of a respective sensing zone reaching a set temperature. In addition, the power source may be configured for alternately generating the heating current and the shielding voltage signal periodically, such as every about 10 to about 50 milliseconds. In other implementations, the period may be every about 10 to about 100 milliseconds.

Furthermore, in certain implementations (not shown), an additional layer of conductive zones for heating the steering wheel may be printed adjacent the same base substrate as the sensing and shielding layers and is separated from the shielding or sensing layer by a dielectric material.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. While implementations will be described for steering wheel hand detection systems, it will become evident to those skilled in the art that the implementations are not limited thereto.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the sensing system for a steering wheel as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting or layering arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present embodiments.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A sensor mat configured for being disposed around a steering wheel frame, the sensor mat comprising:
    a base substrate supporting at least one shielding circuit, at least one sensing circuit, and a plurality of layers of insulating material, wherein the layers of insulating material define a plurality of surfaces in the sensor mat, and wherein the layers are stacked about an axis extending from the base substrate and through the plurality of surfaces;
    one or more of the sensing circuits printed with conductive ink onto one of the plurality of surfaces of the insulating material;
    one or more shielding circuits printed with the conductive ink onto another of the surfaces of insulating material within the sensor mat,
    wherein the shielding circuits and the sensing circuits are configured in corresponding pairs of one shielding circuit and one sensing circuit, wherein the shielding circuits overlap at least one area within the plurality of surfaces of the insulating material on which a respective sensing circuit is printed and such that the shielding circuits and the sensing circuits are separated by at least one of the layers of the insulating material.

2. The sensor mat of claim 1, wherein the base substrate comprises another insulating material and at least one of the sensing circuits or at least one of the shielding circuits is printed onto the base substrate.

3. The sensor mat of claim 1, wherein the plurality of layers of insulating material comprises first and second layers of insulating material and the sensor mat further comprises:
    the one or more shielding circuits are printed with the conductive ink onto the first layer of the insulating material, and
    the second layer of the insulating material disposed over the one or more shielding circuits, wherein the one or more shielding circuits are disposed between the first layer of the insulating material and the second layer of the insulating material.

4. The sensor mat of claim 3, wherein:
    the one or more sensing circuits comprise a first sensing circuit and a second sensing circuit and the one or more shielding circuits comprise a first shielding circuit and a second shielding circuit, and
    the first shielding circuit is disposed adjacent the first sensing circuit and the second shielding circuit is disposed adjacent the second sensing circuit,
    wherein each sensing circuit is a discrete sensing circuit and each shielding circuit is a discrete shielding circuit.

5. The sensor mat of claim 3, wherein:
    the one or more sensing circuits comprise a first sensing circuit and a second sensing circuit and the one or more shielding circuits comprise a first shielding circuit, wherein each sensing circuit is a discrete sensing circuit, and
    the first shielding circuit is disposed adjacent the first and second sensing circuits.

6. The sensor mat of claim 3, further comprising one or more shielding feed traces printed with conductive ink onto the first insulating material, each shielding feed trace extending from a corresponding shielding circuit toward an edge of the first insulating material.

7. The sensor mat of claim 2, further comprising one or more sensor return traces printed with conductive ink onto the base substrate and extending from a corresponding sensing circuit toward an edge of the base substrate.

8. The sensor mat of claim 1, wherein the plurality of layers of insulating material comprises first, second, and third layers of insulating material, and the one or more shielding circuits are printed with conductive ink onto the second layer of the insulating material disposed on the base substrate, wherein the third layer of the insulating material is disposed over the one or more shielding circuits and the one or more sensing circuits are printed onto the third layer of the insulating material, wherein the one or more shielding circuits are disposed between the second layer and third layer of the insulating material.

9. The sensor mat of claim 1, wherein the conductive ink comprises one or more of the following: silver, carbon, carbon nanotube, graphene, zinc, nickel, tin or copper.

10. The sensor mat of claim 9, wherein the conductive ink further includes a polymer additive to affect a resistance of the ink.

11. The sensor mat of claim 1, wherein the conductive ink is capable of withstanding elongation up to about 10%.

12. The sensor mat of claim 11, wherein the base substrate is capable of elongating at least about 20%.

13. The sensor mat of claim 11, wherein the conductive ink is printed in a cross hatch or zigzag pattern.

14. The sensor mat according to claim 1, wherein the base substrate comprises a polymer film and a total thickness of the sensor mat is between about 60 microns to about 185 microns.

15. The sensor mat according to claim 1, wherein the base substrate is an underside of a leather skin configured for being installed around at least a portion of the steering wheel frame rim, and an opposite side of the underside of the leather skin is an outermost layer around the steering wheel frame rim.

16. The sensor mat of claim 1, wherein the ink is printed adjacent the base substrate in a pattern selected from one or more of the following: cross-hatch, zigzag, grid, spiral, or solid area.

17. The sensor mat of claim 1, wherein the base substrate comprises one of the following: a polymer foam, a polymer film, leather, vinyl, felt, or non-woven material.

18. A system for hand sensing in a steering wheel comprising:
   a base substrate supporting at least one shielding circuit, at least one sensing circuit, and a plurality of layers of insulating material, wherein the layers of insulating material define a plurality of surfaces in a sensor mat, and wherein the layers are stacked about an axis extending from the base substrate and through the plurality of surfaces;
   one or more of the sensing circuits printed with conductive ink onto one of the plurality of surfaces of the insulating material;
   one or more shielding circuits printed with the conductive ink onto another of the surfaces of the insulating material within the sensor mat,
   wherein the shielding circuits and the sensing circuits are configured in corresponding pairs of one shielding circuit and one sensing circuit, wherein the shielding circuits overlap at least one area within the plurality of surfaces of the insulating material on which a respective sensing surface is printed and such that the shielding circuits and the sensing circuits are separated by at least one of the layers of the insulating material;
   wherein the sensing circuits and the shielding circuits comprise respective return traces extending across the respective one of the plurality of surfaces and another of the surfaces of the insulating material;
   and
   an electronic control unit in communication with the sensor mat via the return traces, wherein the electronic control unit comprises:
      a processor, and
      a power source,
      wherein the processor is configured for receiving a signal from at least one of the one or more sensing circuits and determining an indication associated with the signal.

19. The system of claim 18, wherein the indication is selected from one of the following: a touch, a tap, hold, swipe, or combination thereof.

20. The system of claim 18, wherein the one or more sensing circuits are printed onto the base substrate.

21. The system of claim 18, wherein the plurality of layers of insulating material comprises first, second, and third layers of the insulating material with the first layer of the insulating material connected to the base substrate, and the one or more shielding circuits are printed with conductive ink onto the second layer of the insulating material disposed on the base substrate, and wherein a third layer of insulating material is disposed over the one or more shielding circuits, and the one or more sensing circuits are printed onto the third layer of insulating material.

22. The system of claim 18, further comprising a corresponding shielding feed trace printed with conductive ink adjacent the base substrate, each shielding feed trace extending from a corresponding shielding circuit toward an edge of the base substrate.

23. The system of claim 22, further comprising a shielding feed wire connected to each shielding feed trace, the shielding feed wire extending between the respective shielding feed trace and the electronic control unit, wherein the processor is configured for instructing the power source to selectively generate a voltage signal through the one or more shielding circuits via the shielding feed wires and the shielding feed traces.

24. The system of claim 18, wherein the one or more shielding circuits are printed with conductive ink adjacent the base substrate and a corresponding shielding feed wire is connected to each shielding circuit, the shielding feed wire extending between the respective shielding circuit and the electronic control unit, wherein the processor is configured for instructing the power source to selectively generate a voltage signal through the one or more shielding circuits via the shielding feed wires.

25. The system of claim 18, further comprising one or more sensor return traces printed with conductive ink adjacent the base substrate, each sensor return trace corresponding to one of the one or more sensing circuits and extending from the respective sensor circuit toward an edge of the base substrate.

26. The system of claim 25, further comprising a sensor return wire extending between each sensor return trace and the electronic control unit, wherein the signal received from at least one of the sensing circuits is received by the processor via the sensor return wire and the sensor return trace.

27. The system of claim 18, further comprising a sensor return wire extending between each sensing circuit and the electronic control unit, wherein the signal received from at least one of the sensing circuits is received by the processor via the sensor return wire.

28. The system of claim 18, wherein the base substrate is a leather skin, and the sensing circuits are printed adjacent an underside of the leather skin, the leather skin is configured to be installed around the steering wheel frame rim, and an outer side of the leather skin opposite the underside is an outermost layer of the steering wheel frame rim.

29. The system of claim 18, wherein a polymeric foam material is disposed between at least a portion of the base substrate and an outermost skin disposed around the steering wheel frame rim.

30. The system of claim 18, wherein a polymeric foam material is disposed between at least a portion of the base substrate and the steering wheel frame rim.

31. A sensor mat configured for being disposed around a steering wheel frame, the sensor mat comprising:
   sensor mat layers defined by a base substrate supporting a plurality of layers of insulating materials thereon;
   a plurality of sensing circuits printed with conductive ink on respective surfaces of the sensor mat layers;
   one or more shielding circuits printed with the conductive ink on at least one other surface of the sensor mat layers, wherein the other surface is not printed with a sensing circuit;
   wherein at least one of the sensing circuits and a corresponding one of the shielding circuits are at least partially aligned along an axis extending from the base substrate and through the plurality of layers of insulating materials;

at least a portion of one of the layers of insulating material separating corresponding pairs of at least one of the sensing circuits and the corresponding one of the shielding circuits;

wherein the conductive ink exhibits an elongation characteristic sufficient to withstand stretching the sensor mat without breaking any circuits when wrapping the sensor mat around a rim of the steering wheel, and wherein the elongation characteristic is expressed as a percentage of elongation relative to a reference force stretching the conductive ink printed on a respective sensor mat layer.

32. A sensor mat according to claim 31, wherein the base substrate exhibits a corresponding elongation characteristic to withstand the stretching of the sensor mat without tearing the base substrate when wrapping the sensor mat around the rim of the steering wheel.

33. A sensor mat according to claim 32, wherein a maximum elongation characteristic of the base substrate overlaps a minimum elongation characteristic of the conductive ink.

* * * * *